(12) United States Patent
Thomson et al.

(10) Patent No.: US 8,779,374 B2
(45) Date of Patent: Jul. 15, 2014

(54) APPARATUS FOR CONTINUOUS IN SITU MONITORING OF ELEMENTAL MERCURY VAPOUR, AND METHOD OF USING SAME

(76) Inventors: Murray J. Thomson, Toronto (CA); Jérôme Thiebaud, San Mateo, CA (US); William H. Morrow, Barrie (CA); Reza Mani, Toronto (CA)

( * ) Notice: Subject to any disclaimer, the term of this patent is extended or adjusted under 35 U.S.C. 154(b) by 479 days.

(21) Appl. No.: 13/138,605

(22) PCT Filed: Mar. 11, 2009

(86) PCT No.: PCT/CA2009/000302
§ 371 (c)(1),
(2), (4) Date: Nov. 17, 2011

(87) PCT Pub. No.: WO2010/102375
PCT Pub. Date: Sep. 16, 2010

(65) Prior Publication Data
US 2012/0161022 A1    Jun. 28, 2012

(51) Int. Cl.
*G01N 21/33*    (2006.01)
(52) U.S. Cl.
USPC ......................................................... 250/372
(58) Field of Classification Search
USPC ................. 250/372, 373, 395, 573, 461.1
See application file for complete search history.

(56) References Cited

U.S. PATENT DOCUMENTS

| | | | |
|---|---|---|---|
| 5,138,175 A * | 8/1992 | Kim et al. | 250/504 R |
| 5,597,535 A | 1/1997 | Schaedlich et al. | |
| 5,679,957 A | 10/1997 | Durham et al. | |
| 5,750,992 A * | 5/1998 | Van Pelt et al. | 250/372 |
| 7,354,553 B2 * | 4/2008 | Appel et al. | 422/91 |
| 8,084,756 B2 * | 12/2011 | Tokhtuev et al. | 250/461.1 |

* cited by examiner

*Primary Examiner* — David Porta
*Assistant Examiner* — Faye Boosalis
(74) *Attorney, Agent, or Firm* — Thorpe North & Western LLP (57) ABSTRACT

An apparatus and method operable for the continuous monitoring of a gas stream including an optical sensor operable to monitor and/or measure Hg concentrations in a flue gas by calculating the absorbance of the ultraviolet light thereby at a range of wavelength 253.7 nm+/−0.05 nm. The apparatus therefore provides as a spectrally narrow UV light source, a mercury lamp. The spectrally broad UV light source includes a UV LED. A 2×2 coupler is provided to mix the narrow and broad UV light energy which is propagated through the gas stream. The invention recognizes that measurement of radiation absorption at the 254 nm+/−1.5 nm range will result in not only from $Hg^0$, but also from the $SO_2$ component in the flue gas. To compensate for sulphur dioxide, measurement of energy absorption for both specially narrow radiant energy in the 253.7 nm+/−0.5 nm range, as well as ultraviolet (UV) light at a comparatively spectrally broad range of 254 nm+/−20 nm is performed recognizing that sulphur dioxide in the emitted flue gas will tend to absorb the ultraviolet light over the broader UV range. Ultraviolet light absorption over the broader range is calculated to provide a correction factor used to correct energy absorption values over the narrow radiant energy range, providing more accurate measurement of the absorption caused by the presence of mercury.

23 Claims, 8 Drawing Sheets

APPARATUS FOR CONTINUOUS IN SITU MONITORING OF ELEMENTAL MERCURY VAPOUR, AND METHOD OF USING SAME

SCOPE OF THE INVENTION

The present invention relates to a method and apparatus for use in the in situ monitoring of mercury, and more preferably a continuous emission monitor (CEM) for in situ monitoring and/or measurement of elemental mercury vapour in a coal-furnace flue gas flow.

BACKGROUND OF THE INVENTION

In the operation of fossil fuel furnaces and power plants which burn oil, coal and/or natural gas, flue gases are discharged into the atmosphere as a by-product of furnace/plant operation. In addition to water vapour, carbon dioxide and nitrogen, flue gases typically contain as products of the fossil fuel consumption, other environmentally harmful substances such as nitrous oxides, sulphur oxides and, particularly in the case of coal-fired plants, fly ash and mercury.

Mercury (Hg) is a known health and ecological concern because it is a toxic, persistent, bioaccumulative substance. The major anthropogenic source of both elemental $Hg^0$ and oxidized Hg arises from coal-based power generation. Once released into the environment, it converts in water to the highly toxic form of methylmercury, which accumulates in fish and other species. In recognition of the deleterious effects of mercury, various governments have proposed increasingly rigid emission standards mandating the capture of mercury from flue gas streams, to reduce the volume of mercury which is introduced into the environment. As a result, there has derived a need to better monitor flue gas mercury content, and in particular the elemental mercury content in coal-furnace flue gases to assess not only the level of mercury released thereby, but also the operating efficiencies of environmental controls and mercury capturing devices.

At present, most mercury level monitoring is performed by wet chemistry analysis using an extractive gas process. Such conventional wet chemistry methods are slow and expensive, involving highly trained staff and the physical removal of a sample volume of gas from the flue gas stream via a conduit pipe. The inventors have appreciated that in addition to difficulties in transferring gas samples for remote analysis, conventional methods suffer a further difficulty in that the physical transfer of the extracted gas sample, inherently provides a delayed response. As a result conventional mercury analysis systems are poorly suited for providing real-time measurement of coal-furnace emissions.

SUMMARY OF THE INVENTION

To at least partially overcome some of the disadvantages associated with prior art devices, the present invention provides an optical based sensor which is positioned for the in situ monitoring and/or measurement of mercury within a combustion furnace flue gas flow. More preferably, the optical sensor provides for real-time monitoring of elemental mercury concentrations in the flue or exhaust gases emitted by coal-fired furnaces, such as those used in coal-fired power plants.

Another object of the invention is to provide an apparatus and method of measuring light absorption as a means of determining mercury concentrations and/or of monitoring mercury vapour in an exhaust or flue gas flow from a fossil fuel-fired furnace.

A further object of the invention is to provide an optical based sensor adapted for in situ placement in a coal-furnace exhaust stack or cooling tower, and more preferably an exhaust stack or tower for a coal-fired power plant furnace, and which is operable to measure and/or monitor contaminate concentrations in flue gases discharged therethrough to assist in providing an indication of environmental control and/or mercury capture efficiencies.

A further object of the invention is to provide an optical sensor which is operable to provide an indication of mercury, and preferably elemental mercury vapour, in a gas stream by measuring ultraviolet (UV) light absorption in the 254 nm+/−1 nm, (253-255 nm) wavelength range across at least part of the stream, and more preferably which compensates for light absorption by other by-products, compounds and/or gases which are co-discharged in the gas stream.

Yet another object of the invention is to provide a simplified apparatus which is operable for the continuous in situ monitoring of mercury in a coal-fired plant flue exhaust stack or tower, and which permits real-time measurement and/or monitoring of mercury, and preferably elemental mercury vapour in the flue gas discharged therethrough during furnace operations.

The present invention relates to an apparatus for measuring and/or monitoring contaminates in a gas stream. More preferably the present apparatus is operable for the monitoring and/or measurement of contaminates such as mercury, and most preferably elemental mercury vapour, in part or all of the gas stream. It is envisioned that in one preferred mode of operation, the apparatus may be used in the real-time or continuous measurement and/or monitoring of elemental mercury ($Hg^0$) concentrations in a waste or exhaust gas stream of a coal-fired furnace, and preferably a flue gas flow of a coal-fired power plant.

As will be described, in a simplest construction, the present invention uses an optical sensor to monitor and/or measure Hg concentrations in the waste gas flow by calculating the amount of ultraviolet light absorbed thereby in a wavelength range selected at about 254 nm+/−1 nm, preferably 253.7 nm+/−0.5 nm, and most preferably 253.7 nm+/−0.01 nm.

In accordance with a preferred method of operation, it has been appreciated that in coal-fired furnace operations, in addition to mercury, discharged flue gases typically also include sulphur dioxide ($SO_2$) as an exhaust component, and which absorbs ultraviolet light over a spectrally broad range, including light energy having wavelengths at about 254 nm+/−20 nm and typically 254 nm+/−15 nm (234-274 nm). The present method therefore recognizes that any measurement of radiation absorption at the 254 nm+/−1 nm range will result in not only from $Hg^0$, but also from the $SO_2$ component in the flue gas. In this regard the method of the invention compensates for the fact that sulphur dioxide in the emitted flue gas will tend to absorb the ultraviolet light over the broader UV range.

To achieve compensation for sulphur dioxide absorption, in one mode, the present invention preferably provides for the measurement of energy absorption of UV light in both spectrally narrow radiant energy in the 253.7+/−0.5 nm range, as well as UV light at a comparatively spectrally broad range of 254+/−20 nm, and typically 254+/−15 to 10 nm range. In implementation, ultraviolet light absorption over the broader range is calculated and used to provide a correction or compensation factor. The correction factor may then be used to correct energy absorption values over the overlapped narrow radiant energy range, providing a more accurate measurement of the absorption caused by mercury in the gas stream.

The degree of absorption attributed to mercury vapour may then correlate to predetermined mercury concentrations on a real-time basis.

It is to be appreciated that in one possible mode, data collected may then be used to provide real-time feedback of mercury capture efficiency or environmental control parameters and/or contaminate output, not only allowing operators to adjust pollutant control operating parameters to maximize the efficiency of environmental control and/or mercury capture operations, but also governmental monitoring authorities.

In one possible construction, the present apparatus provides a spectrally narrow UV light source, a spectrally broad UV light source and a detector assembly used to calculate the amount of UV light energy absorbed. The spectrally narrow UV light source may include a mercury lamp which is operable to emit radiant energy across a spectrally narrow limited wavelength range of about 253.7 nm+/−0.5 nm, preferably 253.7 nm+/−0.05 nm, and most preferably +/−0.01 nm. The spectrally broad UV light preferably includes one or more UV LEDs which are operable to emit spectrally broad UV light energy across a wavelength of about 254 nm+/−20 nm, and typically 254 nm+/−15 nm.

Although not essential, in a simplified construction light energy emitted by the mercury lamp and UV LED light sources are mixed, and attenuated across part or substantially all of a flue gas flow where the transmitted light energy is emitted or reflected onto a suitable collector. The received/returned light is collected and analysed by the detector assembly to measure UV light absorption. The detector assembly is preferably operable to calculate the absorbance of the broad UV spectrum light from the UV LED, to arrive at the proportion of energy absorption which may be attributed to $SO_2$ gas in the flue gas. In particular, by analyzing the degree of absorption of the spectrally broad UV light energy, it is possible to obtain an absorption correction factor which represents UV absorption caused by the presence of $SO_2$ gas in the flue gas flow. The correction factor is then applied to the measured absorption of the light in the spectrally narrow range, effectively removing the effects caused by $SO_2$. This correction factor is thus applied to the calculated absorption value for the spectrally narrow UV light to provide a corrected value which is indicative of UV energy absorption occurring as a result of elemental mercury vapour in the flue gas.

The applicant has appreciated that the present apparatus allows the optical measurement of the flue gas flow directly in a furnace flue exhaust tower, without requiring the physical extraction of a gas sample. As such, the present invention may be operated in situ directly in the stack, providing real-time environmental control monitoring and feedback. Furthermore, the present invention advantageously avoids difficulties associated with conventional extraction probes such as clogging, mercury adherence or absorption to the probe wall, as well as chemical reaction between the probe extraction lines and the sample gases and the like.

Accordingly, in one aspect the present invention resides in an apparatus for the in situ monitoring of elemental mercury vapour in a flue gas flow, comprising a radiant energy source including, a first light source operable to output a first light energy having a wavelength selected at about 253.7 nm+/−1 nm, a second light source operable to output a second light energy having a wavelength selected at about 254 nm+/−20 nm, a light projector lens optically coupled to the radiant energy source and disposed at a first location relative to said flue gas flow, a collector lens assembly disposed at a second location relative said flue gas flow spaced from the first location, a fibre optic connector assembly optically connecting the radiant energy source to said light projector lens, the fibre optic connector assembly including, a first uplead optical fibre optically coupled to the first light source, a second uplead optical fibre optically coupled to the second light source, and an optical coupler optically communicating with the light projector lens and the first and second uplead optical fibres, the optical coupler for mixing input UV light energy from the first and second uplead optical fibres mixed light energy, the projector lens being operable to emit at least part of said mixed light energy as a mixed UV light beam across at least part of said flue gas flow, a detector assembly for measuring reference UV light emitted by said light projector lens, the detector assembly comprising at least one spectrometer for measuring light intensity and/or wavelength received by the collector lens assembly.

In another aspect, the present invention resides in a mercury monitoring apparatus for real time in situ measurement or monitoring of mercury in a coal power plant flue gas flow, comprising a radiant energy source comprising, an Hg lamp operable to output a spectrally narrow first wavelength light energy having a wavelength limited to about 253.7 nm+/−0.05 nm, a UV LED operable to output a spectrally wide second wavelength light energy having a wavelength selected in a range of about 254 nm+/−20 nm, a projector lens optically coupled to the Hg lamp and UV LED and disposed at a first location relative to an exhaust stack for said flue gas flow, the projector lens for propagating a beam of light energy across at least part of the flue gas flow, a collector lens assembly disposed at a second location relative said exhaust stack spaced from said first location, the collector lens positioned to receive the beam of light energy, a fibreoptic connector optically connecting the radiant energy source to said projector lens, the fibreoptic connector including, a 2×2 optical coupler for optically receiving and mixing optical energy from the Hg lamp and UV LED and transmitting mixed optical energy to the projector lens for propagation therefrom as said beam of light energy, a light detector assembly for generally detecting light energy intensity emitted from said projector lens, the light detector assembly including a spectrometer for measuring at least one of light intensity and light wavelength of the beam of light energy emitted by the projector lens as a reference intensity.

In a further aspect, the present invention resides in a method for the in situ monitoring of mercury in coal furnace flue gas flow comprising, providing a first radiant energy output having a narrow UV spectral wavelength selected at about 253.7 nm+/−0.05 nm, providing a second radiant energy output having a broad UV spectral wavelength selected at about 254 nm+/−15 nm, optically mixing the first and second radiant energy outputs as a mixed radiant energy source, propagating the mixed radiant energy source through the flue gas flow from a first location to a second collector location spaced therefrom as a generally columnar beam, measuring the first and second radiant energy output propagated at the first location, measuring the first and second radiant energy output collected at the second location to obtain respective absorption values, correcting the first radiant energy absorption value by a correction value co-related to the second energy absorption value, to obtain a corrected absorption value.

BRIEF DESCRIPTION OF THE DRAWINGS

Reference may now be had to the following detailed description taken together with the accompanying drawings in which.

DETAILED DESCRIPTION OF THE PREFERRED EMBODIMENTS

Figure 1:
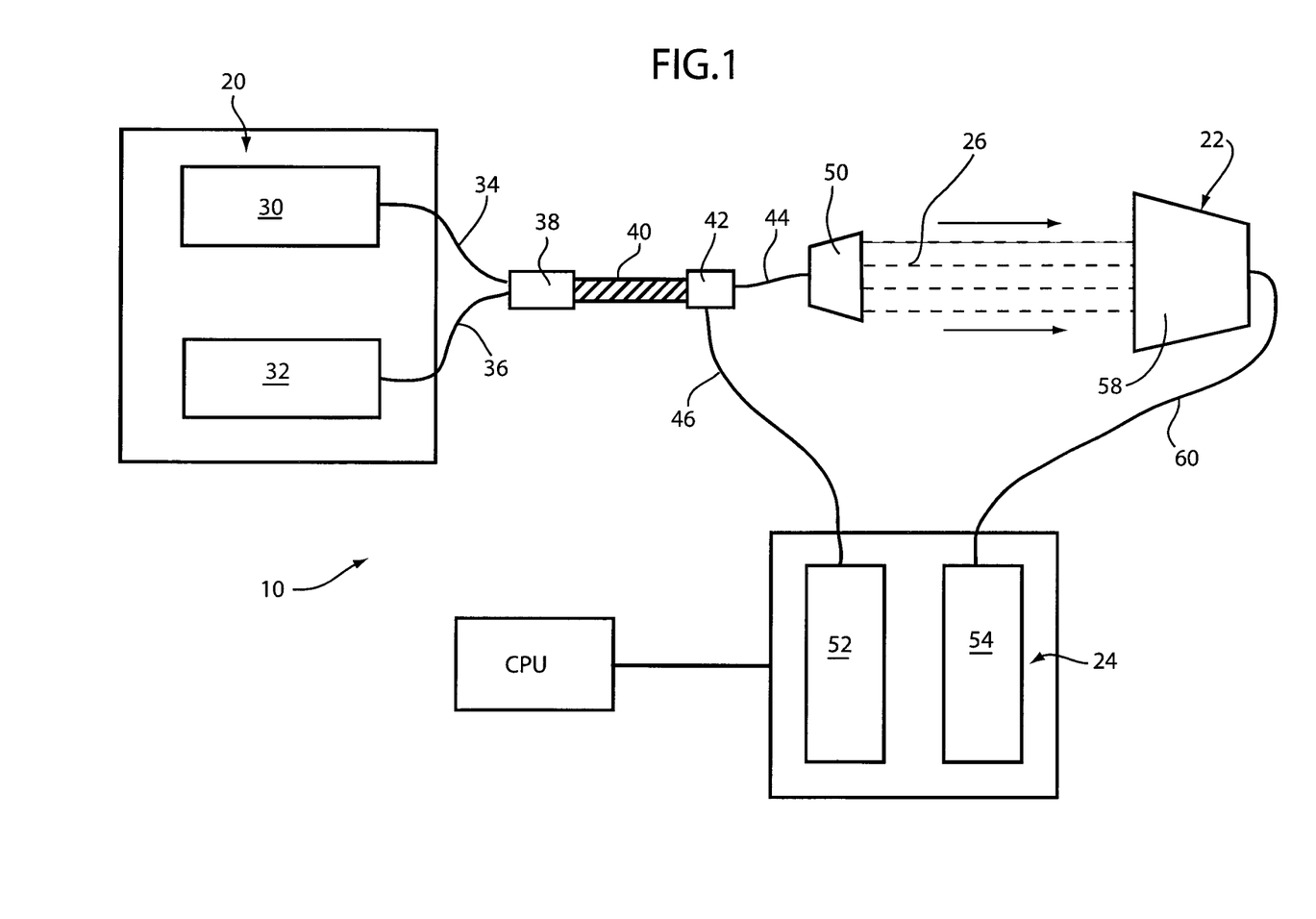
FIG. 1 illustrates schematically an apparatus for the measurement and monitoring of elemental mercury in a flue gas flow in accordance with a preferred embodiment of the invention.
Figure 2:
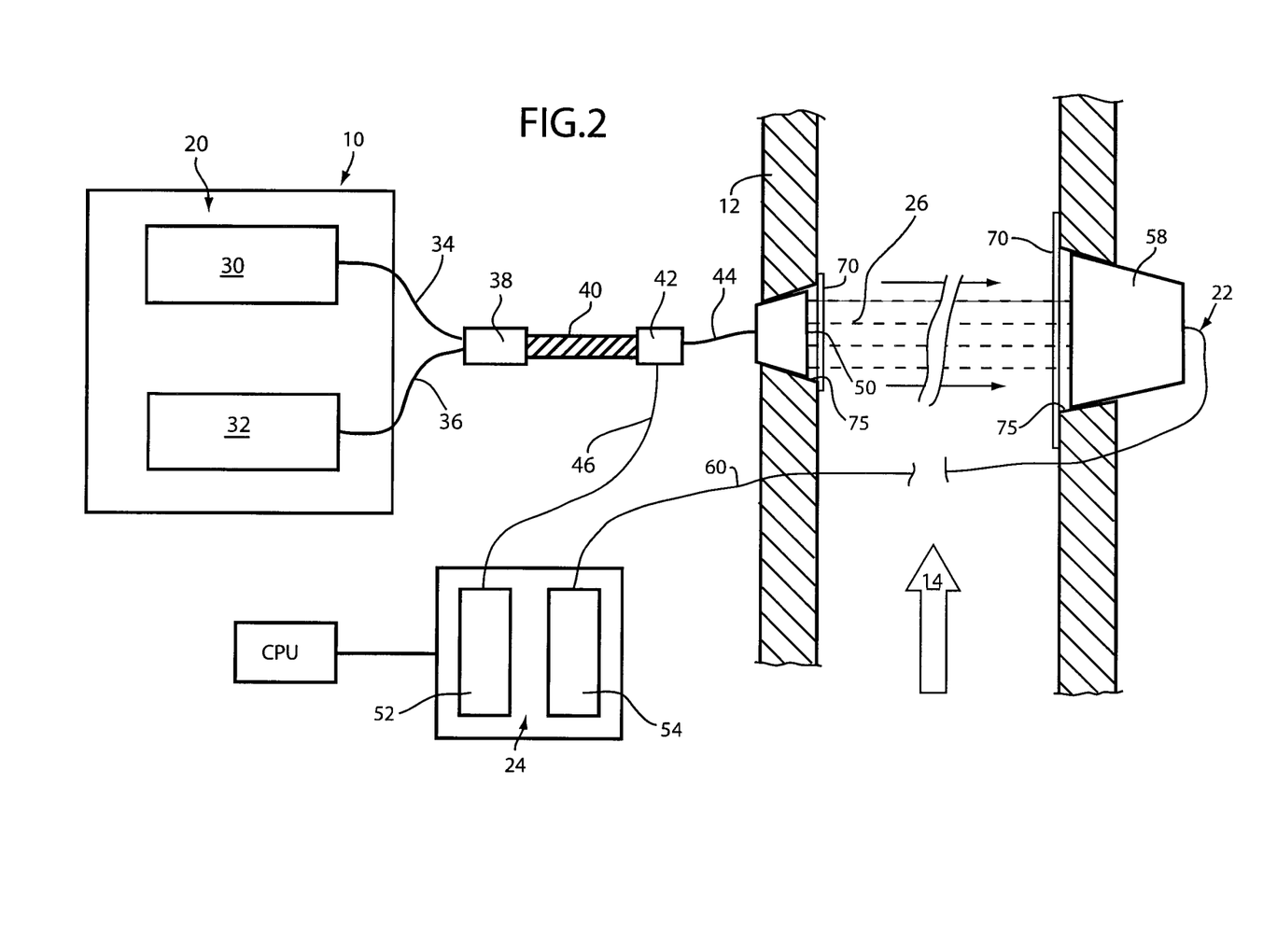
FIG. 2 shows a schematic view of the apparatus of FIG. 1 installed in position in a coal-fired power plant gas exhaust tower for the real-time monitoring of flue gas contaminates.

Reference may be had to FIGS. 1 and 2 which illustrate a continuous emission monitor (CEM) apparatus 10 for use in the real-time in situ monitoring of mercury in accordance with a preferred embodiment of the invention. The apparatus 10 is most preferably provided for installation in a coal-fired power plant exhaust stack 12 (FIG. 2), and operated to provide continuous monitoring of elemental mercury vapour which is discharged as a combustion by-product in a vertically rising furnace flue gas stream or flow 14.

As shown best in FIG. 1, the apparatus 10 includes a radiant energy source 20, a collector lens assembly 22 used to receive and collect non-absorbed radiant energy, and a light detector assembly 24. As will be described, the radiant energy source 20 is operable to emit a light energy beam 26 across the flue gas flow 14, typically in a distance of between about 5 to 10 meters so as to be received by the collector lens assembly 22. As will be described, the detector assembly 24 is then operated to analyze the amount of light energy absorbed by various contaminates in the flue gas flow 14, and providing an indication of the amount of elemental mercury vapour which is entrained in the gas flow 14 and discharged into the environment.

FIG. 1 illustrates best the radiant energy source 20 as including 10 to 50 milliwatt Hg lamp 30, a 0.1 microwatt UV LED 32, and a projector lens 50. The Hg lamp 30 is operable to emit spectrally narrow UV light energy in a limited wavelength range of 253.7 nm+/−0.1 nm, and preferably 253.7 nm+/−0.05 nm. The UV LED 32 may, for example, include a UV TOP™ LED sold by SET Inc., and which is operable to emit spectrally broad UV light energy in a wavelength range 254 nm+/−20 nm, and typically 254 nm+/−15 nm. The Hg lamp 30 and UV LED 32 are optically coupled to a 2×2 optical coupler 38 by respective 0.5 mm diameter fibreoptic uplink cables 34, 36. The 2×2 optical coupler 38 further includes a bifurcated fibre output 40 and a bifurcated connection 42. The output 40 mixes the spectrally narrow and broad UV light energy, and in turn is optically connected to the projector lens 50. The bifurcated connection 42 is interposed at the down lead end of the output 40 towards the projector lens 50. The bifurcated connection 42 provides two fibreoptic outputs 44, 46 and is configured to split therealong the mixed light energy. Most preferably, the connection 42 is selected to split the light energy in a ratio of 9:1 along the outputs 44 and 46, respectively. Preferably, output 44 exhibits a larger diameter then output 46 to maximize the amount of light energy to the projector lens 50.

Figure 8:
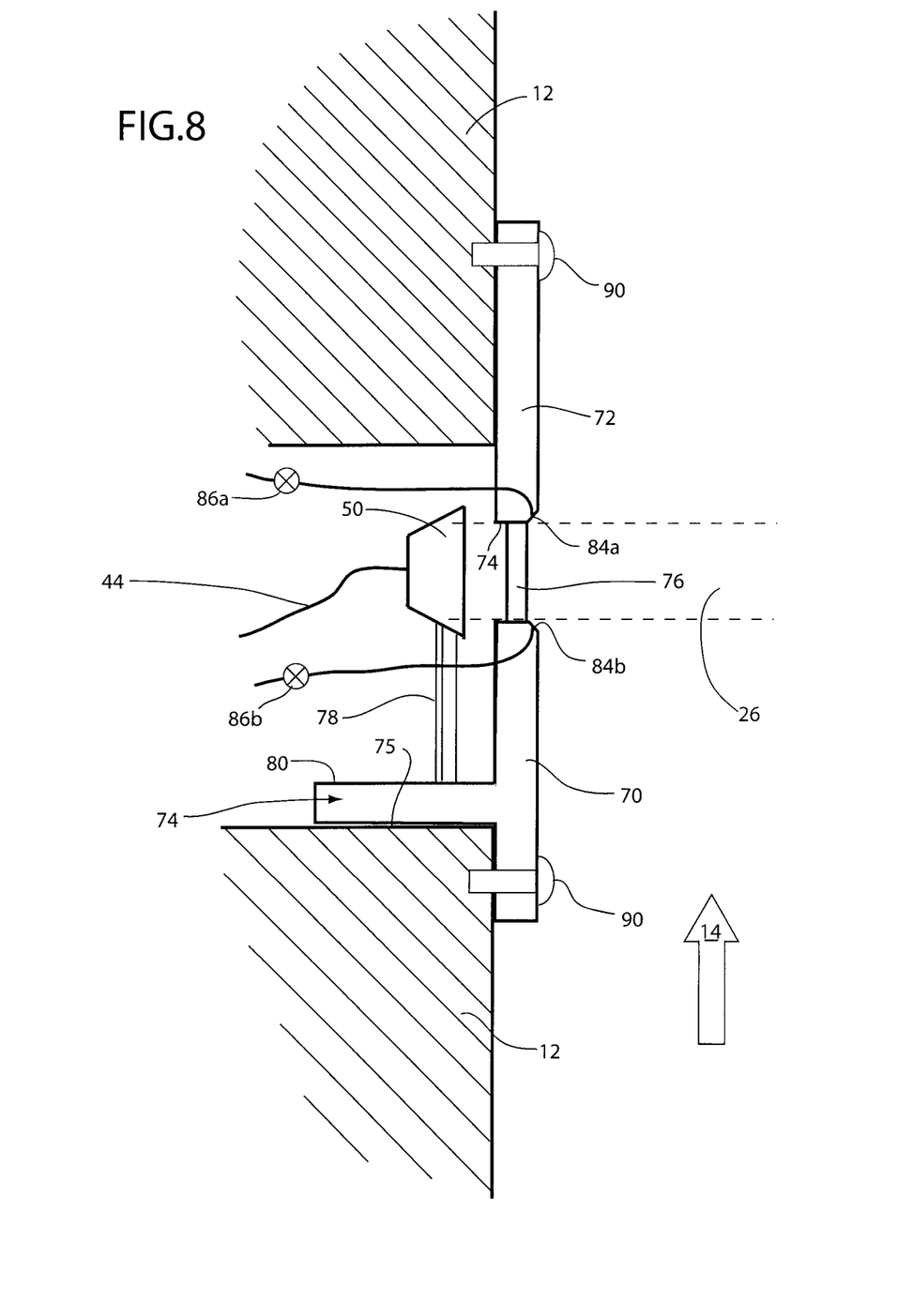
FIG. 8 illustrates schematically a mounting flange assembly used in the flush mounting of an apparatus light projector and collector lens in accordance with a preferred embodiment of the invention.

Fibreoptic output 44 optically connects the output 40 to projector lens 50. Most preferably, the projector lens 50 includes a 75 mm focal length translatable lens used to collimate the mixed narrow and wide UV spectrum radiation as a generally parallel focused UV beam 26. Where the apparatus 10 is used in the monitoring of coal-fired power plant gas stream 14, the projector lens 50 is most preferably flush mounted by way of a mounting flange assembly 70 (FIG. 8) into a recess 75 formed in the sidewall of the exhaust stack 12. Preferably the lens 50 is oriented so as to propagate the light energy beam 26 generally normal to and horizontally through the centre of the flue gas flow 14. FIG. 8 shows best the flange assembly 70 as including a fastening ring 72 having a central circular aperture 74 which is sealed against dust by an optically neutral UV transparent sealing lens 76, and a lens support frame 74. The fastening ring 72 is configured to allow the securement of the flange assembly 70 over the recess 75 by way of bolts 90 or other suitable mechanical fasteners. The lens support frame 74 includes a lens mount 78 used to position the projector lens 50 above a frame base 80 in the desired orientation behind the sealing window 76. Optically a series of air jet outlets 84a, 84b are provided in fluid communication with a pressurized gas source 86a, 86b. The outlets 84 are selectively operable to intermittently or continuously direct a pressurized gas flow against the outer surface of the sealing window 76 to dislodge any dirt or debris from the exhaust gas flow 14 which may accumulate thereon.

FIG. 1 shows best the fibreoptic output 46 as being optically connected to the detector assembly 24. The detector assembly 24 includes at least one, and more preferably two spectrometers 52, 54, with the fibreoptic output 46 operably connected to the spectrometer 52. The spectrometer 52 is in effect operable to measure any variation in optical intensity of the UV energy output by both the Hg lamp 30 and UV LED 32 at the projector lens 50. This output variation measurement therefore provides a reference intensity measurement for the spectrally narrow and broad UV radiant energy which is emitted from the radiant energy source 20, and across the flue gas flow 14 as incident light.

The collector lens assembly 22 most preferably includes a 4 cm diameter UV transparent circular collecting lens 58 and a fibreoptic cable 60. FIG. 2 shows the collecting lens 58 as being mounted in a recess 75 in the sidewall of the exhaust stack 12 at a location directly horizontally and radially opposite to the projector lens 50. It is to be appreciated that the collecting lens 58 is mounted in a recess 75 by way of a flange assembly 70 in substantially the same manner as the projector lens 50. The projector lens 50 is thus configured to propagate the spectrally mixed UV light energy horizontally across the flue gas flow 14 as the optically narrow light energy beam 26 and onto the collecting lens 58. Although not essential, the collecting lens 58 most preferably is flush mounted within the recess 75 or aperture, so as not to otherwise disrupt or interfere with the flue gas flow 14 vertically along the stack 12. The fibreoptic cable 60 may for example consist of a 0.5 mm fibreoptic cable which optically connects the collecting lens 58 to the second spectrometer 54 in the detector assembly 24. In a typical coal-fired power plant application, the projector lens 50 and collector lens 58 are mounted horizontally and radially across from each other where stack 12 has a diameter selected at between about 5 and 10 meters, and typically between about 6 and 8 meters. Although not essential, most preferably the spectrometers 52, 54 are located within 20 meters, and more preferably within approximately 10 meters of the projector lens 50 and collector lens 58, respectively.

In operation, the spectrometer 54 is preferably operable to measure both the intensity and wavelengths of the non-absorbed energy beam 26 which impacts and is received by the lens 58. Each of the spectrometers 52, 54 are operable to provide output data signals to a microprocessor or central processing unit (CPU) 60. The CPU 60 may, by way of non-limiting example, be provided as either part of a central computer control system used to control overall furnace operating parameters, a portable computer such as a laptop used in data collection and/or environmental logging, or alternatively a dedicated microprocessor controller used to regulate scrubbers or flue stack emission controls. As will be described the CPU 60 is operable to determine the $SO_2$ and Hg concentrations in the flue gas flow 14, as a reflection of the amount of UV energy absorbed by the gas flow 14.

Figure 3:
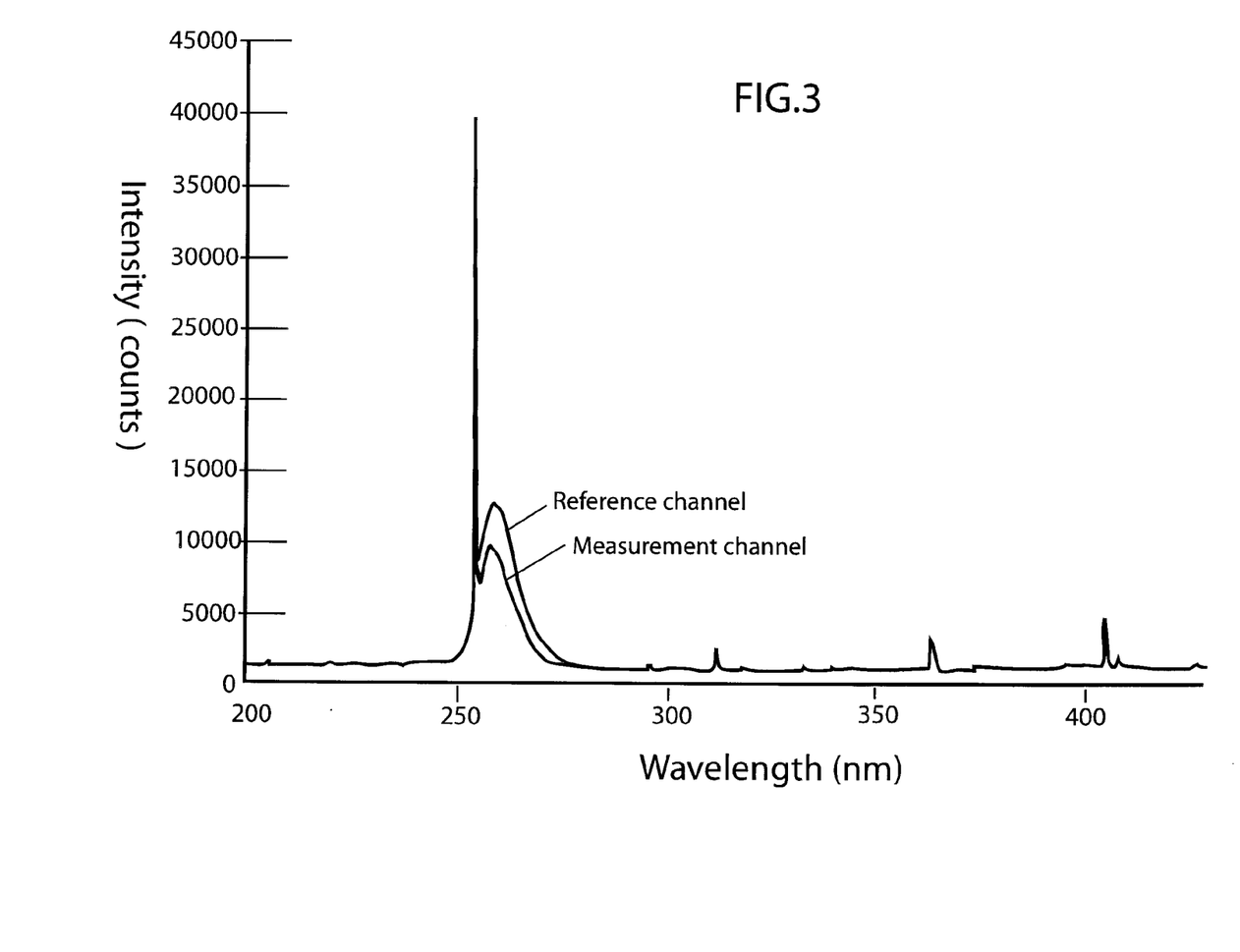
FIG. 3 illustrates graphically energy wavelengths for the spectrally narrow and wide UV light emitted by the radiant light source in the operation of the apparatus of FIG. 1.

To effect the flue gas monitoring, the Hg lamp 30 and LTV LED 32 are activated. As shown best in FIG. 3, once activated the Hg lamp 30 provides a narrow spectrum UV light having a wavelength in the range of approximately 253.7 nm+/−0.1 nm, and preferably 253.7 nm+/−0.05 nm. The UV LED 32 emits relatively spectrally broader UV light having a wavelength range of approximately 254 nm+/−15 nm, and which overlaps the narrow wavelength light emitted by the Hg lamp 30. The emitted light energy is mixed by and attenuated along the bifurcated fibre 40 where it is split into energy beams by the bifurcated connection 42. The split mixed energy beams propagate along the outputs 44, 46 so as to be respectively projected by the lens 50 and horizontally across the direct centre of the flue gas flow 14, and transmitted to the spectrometer 52.

The spectrometer 52 is used to continuously measure variations in optical power of the Hg lamp 30 and UV LED 32 to provide a reference measurement or channel. This reference measurement is preferably used to compensate for any light intensity variations arising from changes in lamp operating parameters (i.e. optical power, temperature, etc.). Simultaneously, the non-absorbed spectrally narrow and non-absorbed spectrally broad UV light energy impacts and is collected by the collector lens 58. The collected UV energy is concurrently and continuously measured by the spectrometer 54 and compared against reference measurements obtained when the furnace is not in operation and flue gases are not present (i.e. when no absorption occurs) [i.e. measurement channel]. The optical losses or UV absorption caused by Hg and $SO_2$ in the flue gas flow 14 are most preferably continuously monitored by the apparatus 10.

By calculating the degree of absorption of the broad spectrum UV light (i.e. the portion of light emitted by the UV LED 32) it is therefore possible to ascertain a correction factor which represents amount of energy absorption caused by the presence of sulphur dioxide in the flue gas flow 14. This absorption factor is then used to correct the absorption readings for the spectrally narrow UV absorption in the 253.7 nm+/−0.05 nm range. The corrected result in effect isolates the proportion of UV energy absorption which is directly attributable to the presence of mercury in the flue gas flow 14. This corrected absorption value is preferably then correlated to preselected values which are indicative of predetermined elemental mercury vapour concentrations for a given flue gas temperature which may be determined experimentally, to provide an indication of the precise Hg content, as for example according to the Beer-Lambert law.

Laboratory and Experiment Results

Figure 4:
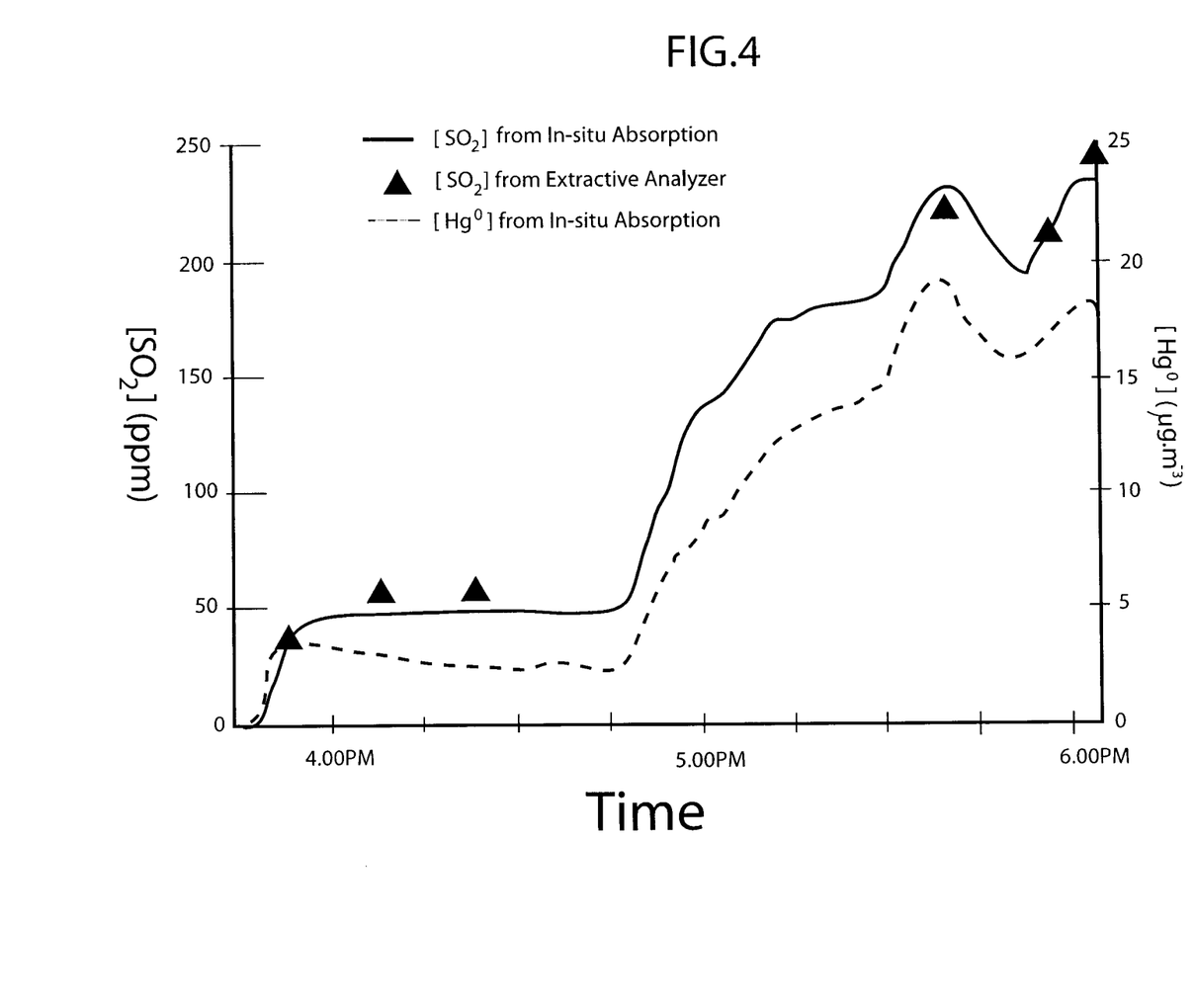
FIG. 4 illustrates graphically concentration profiles for $SO_2$ and $Hg^0$ in a coal-fired power plant furnace flue exhaust gas stream.

Preliminary gas analysis testing, as graphically shown in FIG. 4, suggests that initially during initial coal-furnace operation, during pre-warming of burners by the combustion of natural gas, $SO_2$ absorption levels remain at a plateau. On switching to the consumption of coal, a rapid rise occurs in the levels of both $SO_2$ and $Hg^0$ in the flue gas.

In a laboratory simulation, a test apparatus was established whereby nitrogen gas was selectively fed through either an Hg permeation tube and/or mixed with sulphur dioxide. A UV LED peak and 253.7 nm Hg lamp line were integrated to plot in real-time energy absorption (i.e. intensity area) of each peak versus time. This peak area value, considered as the measured intensity I(t) of each source, produces an absorption value A(t) following the Beer-Lambert relation:

$$\frac{I(t)}{I_0} = e^{-A(t)} \text{ and}$$

$$A(t) = \alpha(t) \times L = C(t) \times \sigma \times L$$

with I(t) the area value measured in real-time; $I_0$ the area value when no absorption; A(t) the absorbance; L the absorption path length in cm and $\alpha(t)$ the absorption coefficient in $cm^{-1}$. The absorption cross-section $\sigma$ is expressed in accordance to the unit used for the absorbing specie concentration C(t). During the test, $SO_2$ was in % so $\sigma_{SO2}$ was in $cm^{-1}$, while $Hg^0$ was in $\mu g \cdot m^{-3}$, leading to $\sigma_{Hg}$ expressed in $cm^2 \cdot \mu g^{-1}$.

As a first test, the response of the sensor to $SO_2$ was measured nitrogen gas flow bypassed the Hg permeation tube to combine with $SO_2$ as the only absorbing specie. The $SO_2$ concentration was increased gradually leading to a stair-shaped signal with each step related to one $SO_2$ concentration value in the gas stream.

Figure 5:
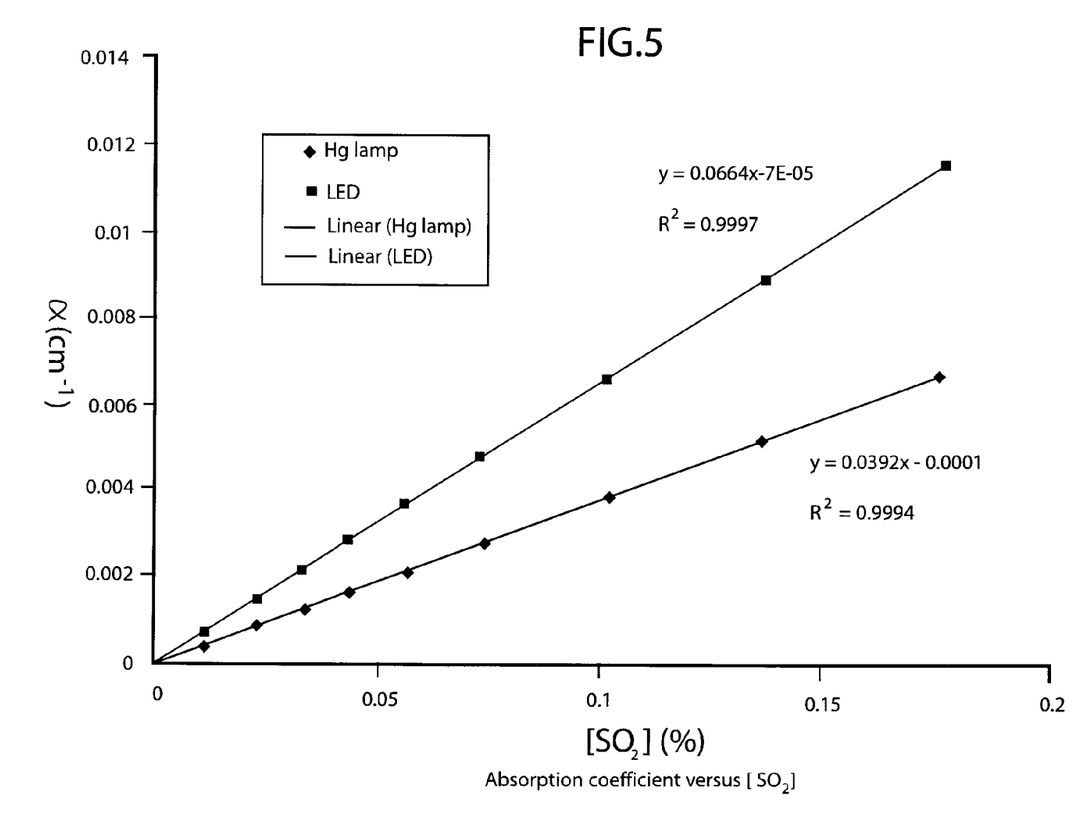
FIG. 5 illustrates graphically absorption coefficient levels for $SO_2$ gas concentration levels for spectrally narrow and broad UV light sources.

FIG. 5 shows the existence of the linear relation between absorption coefficient a and $SO_2$ concentrations. Two different slope values are further shown for both a prototype Hg lamp and the UV LED, wherein the absorption cross-section $\sigma_{SO2,LED}$ for a prototype UV LED is higher than that for the Hg lamp, $\sigma_{SO2,Hglamp}$. This value may in turn be used in $Hg^0$ monitoring in the presence of $SO_2$ concentration; and $SO_2$ concentration factored into a Hg lamp absorbance. The absorbance value due to $SO_2$ can therefore be removed from the total Hg lamp absorbance, with the remaining absorbance attributed to the presence of elemental Hg.

To convert the elemental mercury absorbance values into a concentration value, an absorption cross-section $\sigma_{Hg^0,Hglamp}$ is preferably obtained. An experimental study undertaken with nitrogen gas containing $Hg^0$ alone in the stream at different concentrations. Next $SO_2$ was added, leading to an absorbance offset, and the previous measurement was reiterated by arranging different $Hg^0$ concentrations.

Figure 6:
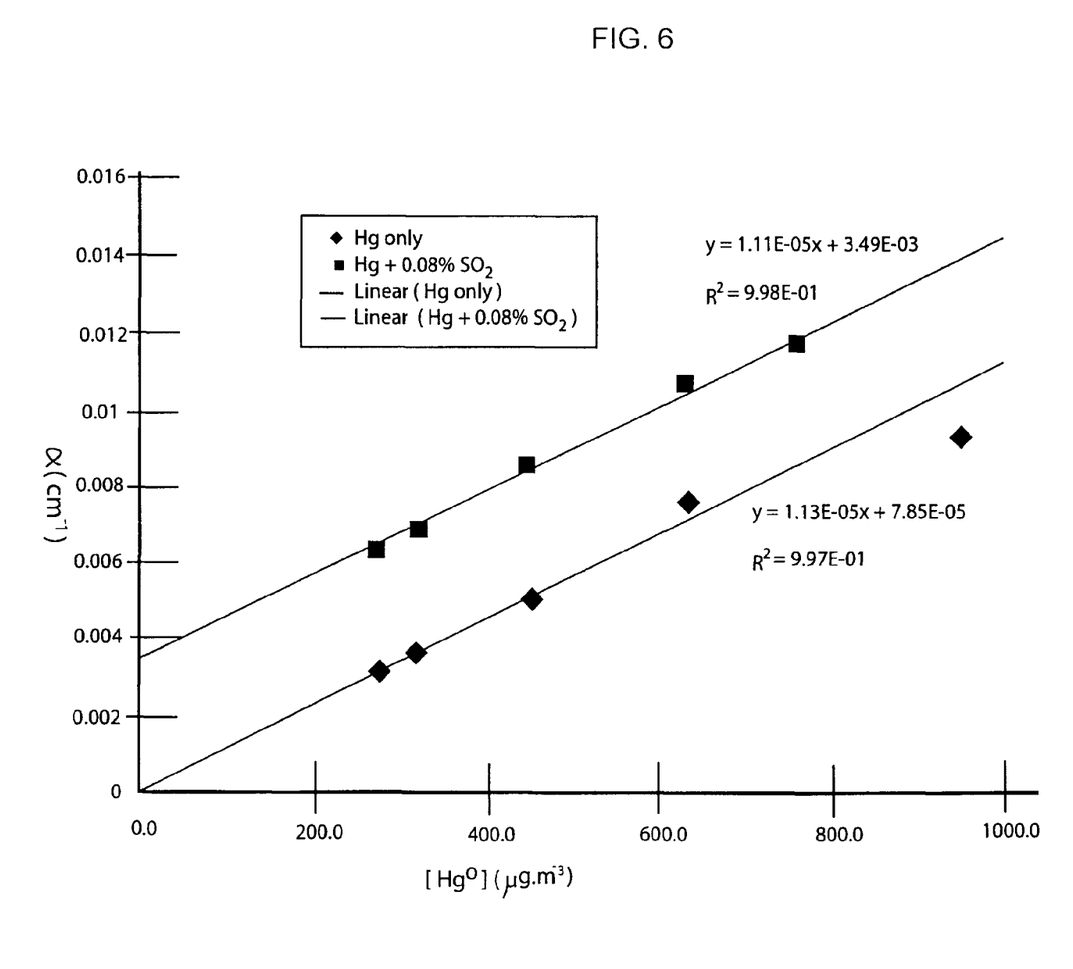
FIG. 6 illustrates graphically absorption coefficient levels for $Hg^0$ only, and $Hg^0$ and 0.08% $SO_2$.
Figure 7:
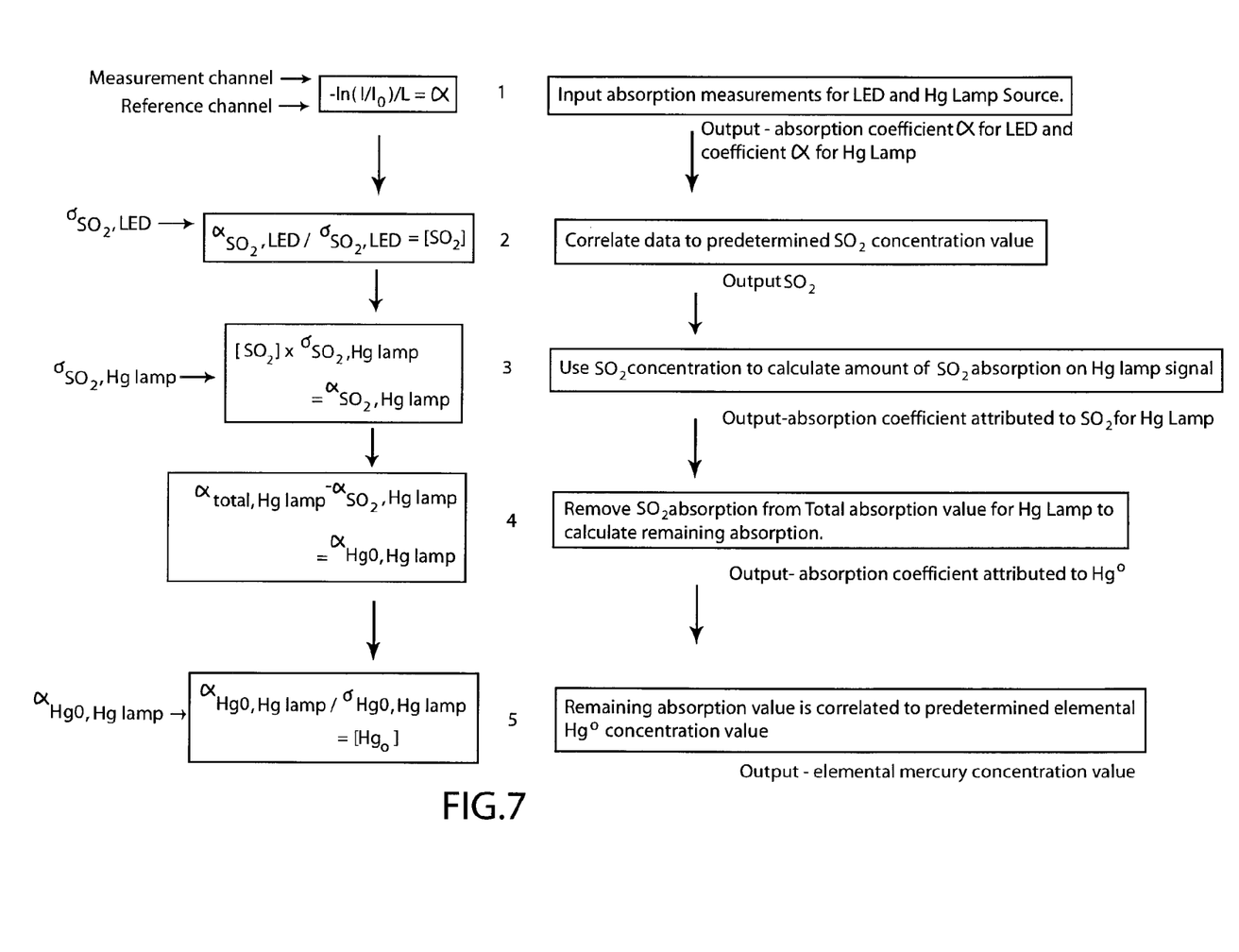
FIG. 7 shows a flow chart illustrating process steps for correcting measured UV energy absorption values in accordance with a preferred method of the invention.

The absorption coefficient plotted versus $Hg^0$ is displayed in FIG. 6. Here only the Hg lamp is considered since the LED gives no response for $Hg^0$. The amount of $SO_2$ induced in an offset does not affect the slope of the linear relation between $Hg^0$ concentration and an absorption coefficient of the Hg lamp. This value allows the conversion of an absorption coefficient due to elemental mercury, and measured with the mercury lamp into an absolute mercury concentration. The procedure thus allows to go from UV LED to Hg lamp intensities detected on both spectrometers, to an absolute elemental mercury concentration $Hg^0$. As is shown in FIG. 7, most preferably the process involves the following steps:

1. Absorption measurements for the UV LED and mercury lamp are input (i.e. UV LED and Hg lamp intensity values, as measured by the spectrometers, absorption cross-sections $\alpha_{LED}$ and $\alpha_{Hglamp}$ are calculated).
2. The absorption coefficient for the combined LED and mercury lamp energy are output, and the data correlated to obtain a predetermined $SO_2$ concentration value (i.e. assuming $\alpha_{LED}=f([SO_2])$ giving the slope $\alpha_{SO2,LED}$ (see FIG. 5), convert the measured $\alpha_{LED}$ value into $SO_2$).
3. The determined $SO_2$ concentration is then output and used to calculate the proportion of the Hg lamp energy which is absorbed by the $SO_2$ (i.e. assuming $\alpha_{Hglamp}=f([SO_2])$ giving the slope $\sigma_{SO2,Hglamp}$ (see FIG. 5), $SO_2$ is converted into $\alpha_{SO2,Hglamp}$).
4. The absorption coefficient for the Hg lamp which is attributed to $SO_2$ is output and removed from the total absorption value for the Hg lamp, leaving the remaining absorption value (i.e. the $SO_2$ contribution is removed from the total Hg lamp absorption coefficient signal, with the remaining signal attributed to $Hg^0$).
5. The remaining absorption value is then correlated to a predetermined elemental $Hg^0$ concentration value (i.e. assuming $\alpha_{Hglamp}=f([Hg^0])$ giving the slope $\sigma_{Hg^0,Hglamp}$ (see FIG. 7), the $\alpha_{Hglamp}$ value is converted into $Hg^0$).

Although the detailed description describes and illustrates the lens 58 of the collector assembly 22 as being positioned on a vertical sidewall of an exhaust stack 12 at a location horizontally and radially opposite to the projector lens 50, the invention is not so limited. It is to be appreciated that in an alternate construction, the projector lens 50 and collector lens 58 could be provided in different positions and/or at alternate locations within the stack 12 without departing from the spirit and scope of the invention. Further, in another construction the projector lens 50 could be configured to both emit the collimated beam and collect UV light reflected by mercury in the flue gas flow 14.

Similarly, while the preferred embodiment describes the use of the apparatus 10 in the analysis of a vertically moving flue gas flow 14, it is understood that the present invention is equally suited for use with horizontally or angularly moving fluid streams.

Although the detailed description describes the apparatus 10 as including a pair of spectrometers 52, 54, it is to be appreciated that in a more economical construction, a single spectrometer 54 could be provided for measuring and/or calculating both reference and measured absorbed UV energy data.

While the preferred embodiments disclose an Hg lamp 30 and UV LED 32 as respectively the light sources for spectrally narrow and spectrally broad ultraviolet light energy, the invention is not so limited. It is to be appreciated that other radiant energy light sources, with or without appropriate light filtering arrangements may also be used.

Although the detailed description describes and illustrates the apparatus 10 as used in the continuous monitoring of a coal-fired power plant flue gas flow 14, the invention is not so limited. It is to be appreciated that the apparatus 10 may also be used to monitor mercury content in exhaust gas flows from a variety of other types of coal or fossil fuel combustion furnaces, and/or in waste incinerator applications where discharge of mercury and/or other contaminates as by-products is of a concern.

Although the detailed description describes and illustrates various preferred embodiments, the invention is not so limited. Many modifications and variations will now occur to persons skilled in the art. For definition of the invention, reference may now be had to the appended claims.

We claim:

1. An apparatus for the in situ monitoring of elemental mercury vapour in a flue gas flow, comprising,
   a radiant energy source including,
   a first light source operable to output a first light energy having a wavelength selected at about 253.7 nm+/−1 nm,
   a second light source operable to output a second light energy having a wavelength selected at about 254 nm+/− 20 nm,
   a light projector lens optically coupled to the radiant energy source and disposed at a first location relative to said flue gas flow,
   a collector lens assembly disposed at a second location relative said flue gas flow spaced from the first location,
   a fibreoptic connector assembly optically connecting the radiant energy source to said light projector lens, the fibreoptic connector assembly including,
   a first uplead optical fibre optically coupled to the first light source,
   a second uplead optical fibre optically coupled to the second light source, and
   an optical coupler optically communicating with the light projector lens and the first and second uplead optical fibres, the optical coupler for mixing input UV light energy from the first and second uplead optical fibres and transmitting mixed light energy to the projector lens,
   the projector lens being operable to emit at least part of said mixed light energy as a mixed UV light beam across at least part of said flue gas flow,
   the collector lens assembly operable to receive the mixed UV light beam emitted across said at least part of the flue gas flow,
   a detector assembly for measuring reference UV light emitted by said light projector lens, the detector assembly comprising at least one spectrometer for measuring at least one of light intensity and light wavelength received by the collector lens assembly.

2. The apparatus of claim 1 further wherein the optical coupler comprises a 2×2 optical coupler and further includes an optical splitter coupled to each of said projector lens and said spectrometer, the optical splitter operable for splitting the mixed light energy between the projector lens and the spectrometer, whereby said detector assembly is operable to measure variations in at least one of light intensity and light wavelength emitted by said radiant energy source.

3. The apparatus of claim 2, wherein the 2×2 couple further comprises a bifurcated connection for dividing said input UV light energy into said beam of mixed light energy and said reference UV light.

4. The apparatus of claim 1, wherein the second light source comprises at least one ultraviolet LED.

5. The apparatus of claim 1, wherein the first light source is operable to output light energy limited along a spectrally narrow wavelength selected at 253.7 nm+/−0.5 nm.

6. The apparatus of claim 1, wherein the first light source comprises at least one mercury lamp.

7. The apparatus of claim 1, wherein the flue gas comprises a coal-fired furnace flue gas, and the first location comprises a first peripheral side of said flue gas flow, and said second location comprises a second peripheral side of the flue gas flow generally radially opposite to said first location.

8. The apparatus of claim 1, wherein the apparatus comprises flue gas stack monitoring apparatus for a coal-fired power plant, and said first location comprises a first peripheral side of a flue gas exhaust stack, and the second location comprises a second peripheral side of the exhaust stack horizontally opposite to said first location.

9. The apparatus as claimed in claim 1, wherein the first light source comprises an Hg lamp operable to output spectrally narrow light energy having a wavelength selected in a range limited to about 253.7 nm+/−0.1 nm, and said second light energy has a wavelength selected in a range of about 254 nm+/−15 nm.

10. The apparatus as claimed in claim 1, wherein said light projector lens comprises a 2 to 4 cm diameter UV transparent collimating lens and said mixed UV light beam comprises a 0.1 to 20 cm diameter collimated beam.

11. The apparatus as claimed in claim 1, wherein the light projector lens is positioned to propagate said mixed UV light beam generally across a mid-portion of said flue gas flow.

12. The apparatus of claim 1, wherein the collector lens assembly comprises a 3 to 6 cm diameter UV transparent lens, a fibreoptic cable optically communicating the collector lens assembly to a spectrometer for measuring at least one of light intensity and light wavelength of non-absorbed UV energy which attenuates through said flue gas flow.

13. The apparatus as claimed in claim 1, further wherein the detector spectrometer is operable to measure UV light which is incident on said collector lens in the absence of said flue gas flow for measuring an emitted light intensity and/or wavelength projected into the flue gas flow from the projecting lens.

14. A method of using the apparatus as claimed in claim 1, comprising,
comparing an intensity of the second light energy emitted at the light projector lens to an intensity of the second light energy received by the collector lens assembly to determine a total UV absorption loss value,
comparing an intensity of the first light energy emitted at the projector lens to an intensity of the first light energy received by the collector lens assembly to determine a total absorption value, and
correcting the total absorption value of said first light energy by the total UV absorption loss value, to provide a corrected Hg absorption value.

15. The method of claim 14 further monitoring as a reference measurement variations in first and second light energy output, and wherein the corrected Hg absorption value is compared to one or more preselected values indicative of a predetermined elemental mercury vapour concentration.

16. Use of the apparatus of claim 1, wherein,
comparing a detected first light energy intensity in the mixed UV light beam received by the collector lens assembly to a detected first light energy intensity in the mixed UV light beam emitted by the projector lens to determine a measurement of total radiation Mercury/Sulphur dioxide [$Hg^0/SO_2$] absorption in the flue gas flow,
comparing a detected second light energy intensity in the mixed UV light beam received by the collector lens assembly to a detected second light energy intensity in the mixed UV light beam emitted by the light projector lens to determine a correction factor representative of $SO_2$ concentration in the flue gas stream, and adjusting the total radiation $Hg^0/SO_2$ absorption value by the correction factor to provide a corrected absorption value indicative of $Hg^0$ absorption.

17. Use of the apparatus as claimed in claim 16 further comprising comparing the corrected absorption value with a plurality of predetermined values which are each indicative of a selected elemental mercury vapour concentration.

18. The apparatus as claimed in claim 1, further including at least one mounting flange assembly for mounting said projector lens, the mounting flange assembly including a substantially UV transparent sealing window for substantially isolating said projector lens from the flue gas flow, and at least one gas nozzle for directing a fluid flow gas against said sealing window to dislodge dirt or debris which has accumulated thereon.

19. The apparatus as claimed in claim 1, wherein the flue gas flow comprises a gas flow from a combustion furnace selected from the group consisting of a coal-fired power plant furnace and a waste incinerator.

20. A mercury monitoring apparatus for real-time in situ measurement or monitoring of mercury in a coal power plant flue gas flow along an exhaust stack, comprising,
a radiant energy source comprising,
an Hg lamp operable to output a spectrally narrow first wavelength light energy having a wavelength limited to about 253.7 nm+/−0.05 nm,
a UV LED operable to output a spectrally wide second wavelength light energy having a wavelength selected in a range of about 254 nm+/−20 nm,
a projector lens optically coupled to the Hg lamp and UV LED and disposed at a first location relative to the exhaust stack for said flue gas flow, the projector lens for propagating a beam of light energy across at least part of the flue gas flow in the exhaust stack,
a collector lens assembly disposed at a second location relative said exhaust stack spaced from said first location, the collector lens positioned to receive the beam of light energy propagated across the part of the flue gas flow,
a fibreoptic connector optically connecting the radiant energy source to said projector lens, the fibreoptic connector including,
a 2×2 optical coupler for optically receiving and mixing optical energy from the Hg lamp and UV LED and transmitting mixed optical energy to the projector lens for propagation therefrom as said beam of light energy,
a light detector assembly for generally detecting light energy intensity emitted from said projector lens, the light detector assembly including a spectrometer for measuring at least one of light intensity and light wavelength of the beam of light energy emitted by the projector lens as a reference intensity.

21. A mercury monitoring apparatus as claimed in claim 20 wherein the light detector assembly is operable to separately measure the intensity of the first and second wavelength light energy in the beam of light energy emitted by the projector lens substantially in the absence of said flue gas flow, and the measured intensity of the first and second wavelength energy in the beam of light energy received by the collector lens across said flue gas flow, and providing a correction absorption value for the measured first wavelength light energy which is dependent on the difference between the measured intensity of the second wavelength light energy.

22. A method for the in situ monitoring of mercury in coal furnace flue gas flow along an exhaust stack comprising,
providing a first radiant energy output having a narrow UV spectral wavelength limited at about 253.7 nm+/−0.05 nm,
providing a second radiant energy output having a broad UV spectral wavelength selected at about 254 nm+/−15 nm,
optically mixing the first and second radiant energy outputs as a mixed radiant energy source, propagating the mixed radiant energy source through the flue gas flow from a first location along said exhaust stack to a second collector location spaced therefrom as a generally columnar beam, measuring the first and second radiant energy output propagated at the first location, measuring the first and second radiant energy output collected at the second location to obtain respective absorption values, correcting the first radiant energy absorption value by a correction value co-related to the second energy absorption value, to obtain a corrected absorption value.

23. The method of claim 22, wherein the correction absorption value is compared to a series of absorption values indicative a respective predetermined elemental mercury vapour concentration.

* * * * *